Figure 6:
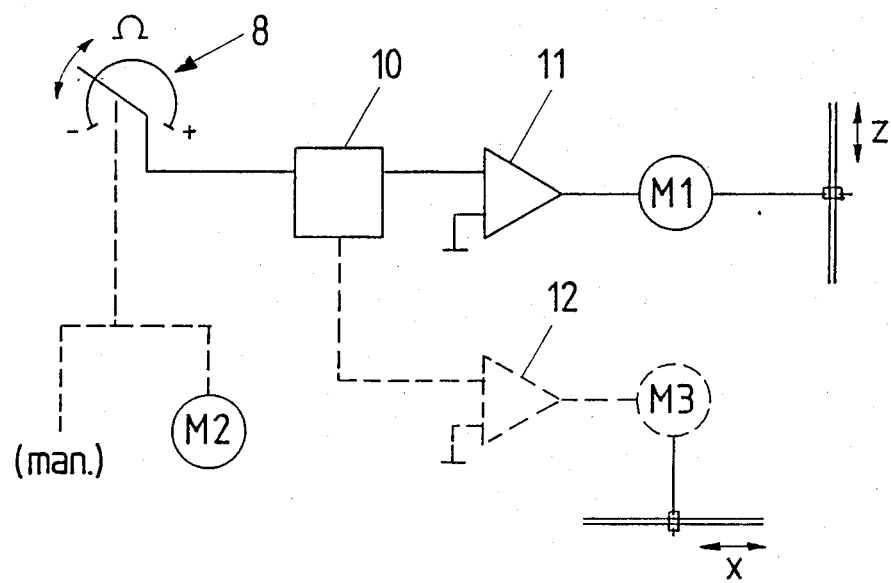

United States Patent [19]

Mikkonen et al.

[11] Patent Number: 4,910,756
[45] Date of Patent: Mar. 20, 1990

[54] MAMMOGRAPHY

[75] Inventors: Hannu Mikkonen, Vantaa; Tuomas Kyllönen, Espoo, both of Finland

[73] Assignee: Orion - Yhtyma Oy, Helsinki, Finland

[21] Appl. No.: 295,309

[22] Filed: Jan. 10, 1989

[30] Foreign Application Priority Data

Jan. 11, 1988 [FI] Finland .................................. 880106

[51] Int. Cl.$^4$ .............................................. A61B 6/04
[52] U.S. Cl. ...................................... 378/37; 378/196
[58] Field of Search .................. 378/37, 196, 179, 180

[56] References Cited

U.S. PATENT DOCUMENTS 3,609,355 9/1971 Schwarzer ............................ 378/37

Primary Examiner—Craig E. Church
Attorney, Agent, or Firm—Bucknam and Archer

[57] ABSTRACT

The invention relates to a mammography device, having a frame column (3) comprising a slide (2) mounted vertically (Z) slidingly onto bearings, into the horizontal axis of which the photography head (1) is pivotally mounted onto bearings. According to the invention, the control device (10), the photography head (1) being tilted, guides the hoisting mechanism (M1) of the slide (2) according to a preset program and to the observed angle of inclination ($\Omega$) in such a way that the center point of the support plate (6) in the photography head is at essentially the same height above the support (20) at the end of the tilting movement.

3 Claims, 2 Drawing Sheets

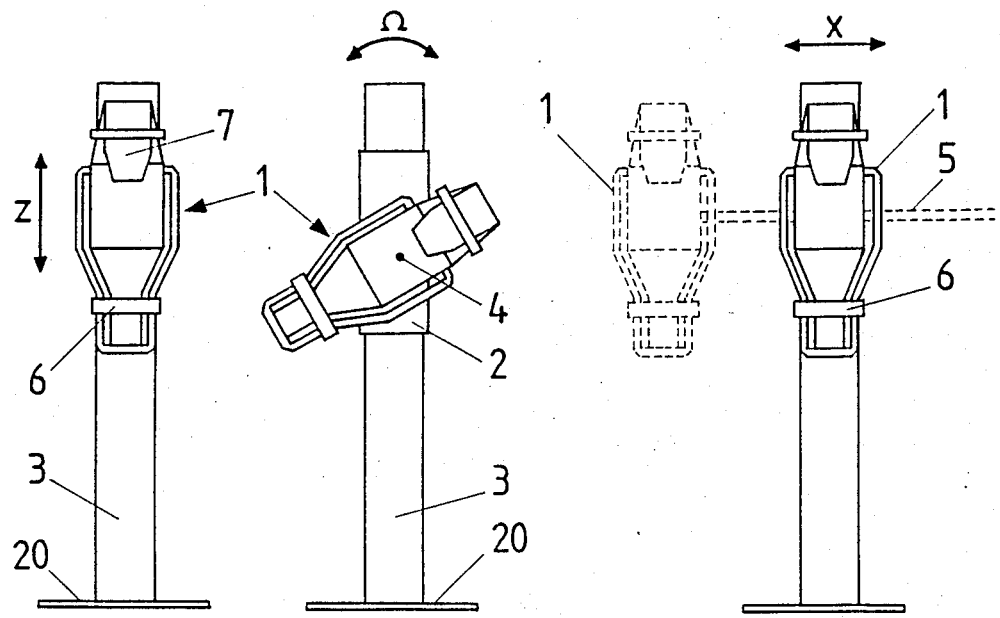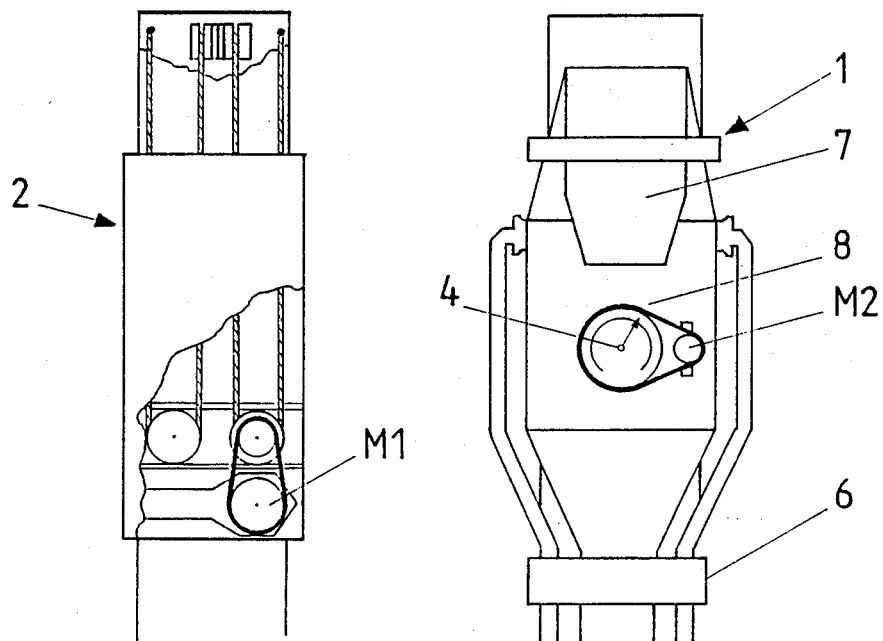

MAMMOGRAPHY

The invention relates to a type of device for mammography.

In mammography devices, the breast to be photographed is X-rayed both vertically and with the photography head being inclined. In known devices, the displacing of the photography head is done manually or under manual control by means of a motor. The object to be photographed is placed on the support plate of the photography head, the height position of which having been appropriately adjusted. When inclining the photography head, the centre point of the support plate moves on a circumference, the centre point of which is the rotation axis of the photography head, whereby the centre point rises to a higher position. In order to provide the proper support for the photographed breast, the support plate has to be lowered. This is done by lowering the slide of the photography head, which is usually done by manually adjustment.

The above tilting operation and the connected height adjustment of the slide are time-consuming measures that require great precision, which are simplified by the present invention.

The present invention is illustrated by reference to the drawings of which:

FIG. 1 shows a mammography device according to the invention, the height of which is vertically adjustable as shown by the symbols Z;

FIG. 2 shows the device of FIG. 1, which can be inclined (in the angle $\Omega$) from the vertical direction (the tilting shown in the figure is done without automatic height compensation); FIG. 3 is a schematic partial section view of the hoisting mechanism M1 of the slide of the device according to the invention; FIG. 4 is a schematic presentation of the tilting mechanism M2 of the photography head of the device according to the invention; FIG. 5 illustrates an option embodiment of the device according to the invention, in which the photography head is horizontally displaceable as shown by the symbol X (the horizontally displaced photography head is indicated by dotted lines); FIG. 6 is a schematic view of the control system of the device according to the invention.

The mammography device stands on the support 20. According to figure 1, the column 3 of the device supports the slide 2 of the photography head, which is slidingly mounted onto bearings on the column and the upper end of which comprises an X-ray source 7 and the lower end a support plate 6. The height of the slide is adjusted by the actuator M1 (FIG. 3). FIG. 2 shows the inclination of the photography head about the axis 4 in the slide (cf. also FIG. 4), whereby the angle of inclination $\Omega$ with regard to the vertical plane can be as large as $\pm 100°$. The inclination can be guided either manually or by means of the actuator M2.

The breast object to photographing is placed on the support base 6, the slide having first been adjusted to the proper height. When needed, a height correcting adjustment can be carried out depending on the patient. Before the photographing, the breast is slightly compressed into position by means of a compression plate (not shown). The radiation source (X-ray source) 7 is disposed in the photographing head above the breast and the recording means, the film, is disposed in the support plate or underneath the support plate 6.

If desired, the photography head can be tilted, e.g. 45°, the actual angle of inclination being detected by the detector 8 shown in FIG. 4, e.g. a potentiometer. When comparing the positions of the photography head in FIGS. 1 and 2, it can be observed that without the height compensation of the photography head (FIG. 2) the support plate rises to a higher position, when the photography head is being tilted. By connecting the communication from the angle detector 8 to the control device 10 according to FIG. 6, a communication is obtained in the output of the guide device 10 according to the preset program, which is proportional to the angle $\Omega$, and by means of which the actuator M1 is guided via the amplifier 11 in order to adjust the height Z of the photography head, In this manner, the centre point of the support plate 6 is maintained on the same height level with regard to the support 20, regardless of the angle $\Omega$. Optionally, instead of direct proportionality, the control device 10 can be given a form factor/form function describing the shape of the photographed breast, according to which the height position of the support plate is corrected so that it conforms still better to the outline of the cross-section of the base of the breast.

The control device can also comprise a connection, by means of which the tilting motor M2 is controlled according to a specific program or instruction. This is not shown in the figure. In the embodiment of FIG. 5 the device is further provided with an actuator M3 displacing the photography head horizontally X and with a support arm 5. On the basis of the inclination angle $\Omega$ the actuator M3 can be guided via the amplifier 12 according to the program on the control device 10. The horizontal movement can be guided so as to maintain the central point of the support plate 6 essentially on the same vertical line. Optionally, the photography head can be horizontally displaced so that the support plate conforms optimally to the outline of the cross-section of the base of the breast.

We claim:

1. A mammography apparatus which comprises a platform (20), a supporting column (3) mounted on said platform and projecting upwardly therefrom, said column (3) having bearings, a photography head (1) having a slide member (2), said slide member being mounted in said bearings on said supporting column (3) and vertically movable therealong, a support plate (6) positioned in the lower part of said photography head; said photography head (1) being mounted tiltably on said slide member on a substantially horizontal axis (4) whereby said photography head may be inclined according to an angle of $\pm$ 100 degrees, and when said photography head is inclined, said support plate (6) rising to a higher position, a radiation source (7) positioned in the upper part of said photography head; said photography head having an initial position, wherein said radiation source is positioned vertically above and said support plate is positioned vertically under said horizontal axis; hoisting means (M1) for effecting vertical movement of said slide member; tilting means (M2) for effecting pivotal movement of the photography head around its horizontal axis, and control means (10) for controlling said hoisting means according to the angle of inclination in order to maintain a centre point of said support plate (6) at a constant chosen vertical level with respect to said platform (20), irrespective of the pivotal movement of the photography head.

2. A mammography device according to claim 1, comprising motor means (M3) for displacing the photography head horizontally according to a preset program and to the observed angle of inclination thereof, said control means also controlling said motor means in order to retain said centre point of the support plate during the tilting movement.

3. A mammography device according to claim 1, wherein said control means is disposed to guide also said tilting means according to a preset program.

* * * * *